United States Patent [19]

Greenberg

[11] 4,107,342
[45] Aug. 15, 1978

[54] FLAVORING WITH 1,7-DIHYDROXY-2,5-DITHIA-TRICYCLO[7.3.0.0³,⁷]DODECANE

[75] Inventor: Michael J. Greenberg, Chicago, Ill.

[73] Assignee: The Quaker Oats Company, Chicago, Ill.

[21] Appl. No.: 836,775

[22] Filed: Sep. 26, 1977

Related U.S. Application Data

[62] Division of Ser. No. 769,520, Feb. 17, 1977.

[51] Int. Cl.² .............................................. A23L 1/231
[52] U.S. Cl. ................................................... 426/535
[58] Field of Search ................... 426/535; 260/327 P

[56] References Cited

U.S. PATENT DOCUMENTS

| | | | |
|---|---|---|---|
| 2,955,041 | 10/1960 | Broderick et al. | 426/535 |
| 3,773,524 | 11/1973 | Katz et al. | 426/535 |
| 3,863,013 | 1/1975 | Wilson et al. | 426/535 |
| 3,876,809 | 4/1975 | Mussinan et al. | 426/535 |

OTHER PUBLICATIONS

Chem. Abstracts, vol. 61, 1964, 1854e.
Chem. Abstracts, vol. 52, 1958, 1174i.

*Primary Examiner*—Joseph M. Golian
*Attorney, Agent, or Firm*—Mathew R. P. Perrone, Jr.

[57] ABSTRACT

Flavors in foods are enhanced by addition to the

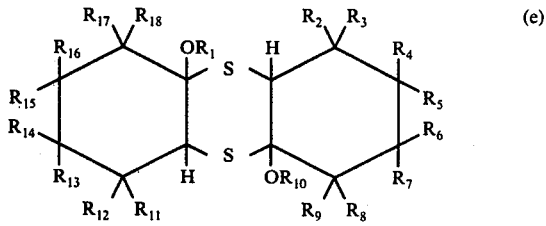

food of 1,7-dihydroxy-2,8-dithia tricyclo[7.3.0.0³,⁷]dodecane having the formula:

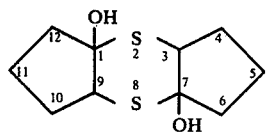

7 Claims, No Drawings

FLAVORING WITH 1,7-DIHYDROXY-2,5-DITHIA-TRICYCLO[7.3.0.0³,⁷]DODECANE

CROSS-REFERENCE TO RELATED APPLICATION

This application is a divisional application of U.S. Ser. No. 769,520, filed Feb. 17, 1977.

BACKGROUND OF THE INVENTION

This invention relates to foods; and more particularly to flavored foods, and specifically pet foods, having added thereto thermally stable 1,8-dihydroxy-2,9-dithia-tricyclo [8.4.0.0³,⁸]tetradecane and its derivatives as flavorants. Also 1,7-dihydroxy-2,8-dithia-tricyclo[7.3.0.0³,⁷]dodecane and derivatives thereof may be used as flavorants.

The consumption of food involves many complex factors. Consumption is always affected by supply. Further complicating the food supply is that food must not only be edible, it must also be acceptable to the consumer. This acceptability to the consumer involves many complex factors. Added to these factors are the complications of custom and national tradition that distinguish and interfere with the consumption of otherwise edible material. In other words, not only is the food supply short, some of the food which is available, nutritional and edible is still unacceptable. This unacceptability is due in part, to the organoleptic property of the food known as flavor. Flavor is basically associated with the taste, aroma, appearance, and texture of foodstuffs. The taste and aroma aspect of a flavorant are major variables in determining the acceptability of a foodstuff.

Much research time, skill, and money are devoted to the development of suitable flavors which can then be used to render acceptable those edible materials or foods which are otherwise unacceptable. Flavorants can render foods more acceptable from both a taste and aroma standpoint. Additionally, flavorants can help a particular food maintain its natural aroma and avoid flavor deterioration. These advantages for flavorants justify the time spent in determining suitable flavorants.

Flavorants have contrasting requirements of thermal stability and volatility. Aroma stability is required so that both the aroma and the desired taste will remain with the food for a sufficient time to achieve the desired effect of making the food more acceptable. Volatility is required so that the aroma of the flavorant will in some way indicate its presence in the food and perform the desired function of making it more acceptable to the consumer. However, the more volatile a flavorant is, the shorter period of time it will provide the pleasing aroma. On the other hand, the more thermally stable a flavorant is, the less volatile it becomes and more is required to give a pleasing aroma. These contrasting desirable features must be balanced in order to achieve an effective flavorant.

In addition to having the desired volatility and long term thermal stability, the flavorant must also be capable of surviving hydrolytic conditions and strenuous food processing conditions. These conditions can be extremely strenuous and have an adverse affect on a compound which must be volatile. Thus, the incorporation of this desired flavorant into a food may cause problems in the formulation of a food containing the flavorant.

Food as used herein is well defined in the prior art. U.S. Pat. No. 3,876,809 to Mussinan et al. (incorporated herein by reference) clearly defines food and the purposes thereof. Flavorants provide organoleptic acceptability for foods. Since meat is a most acceptable form of protein food, it is extremely desirable to provide both the taste and aroma of meat to be added to protein containing foods. In this fashion, protein containing foods not having a meat flavor may be made more acceptable to the consumer.

Among the desired flavoring agents in foodstuffs are the 2,5 dihydroxy-1,4-dithianes[a] and the dimethyl[b] and diethyl[c] alkyl-dihydroxy dithianes.

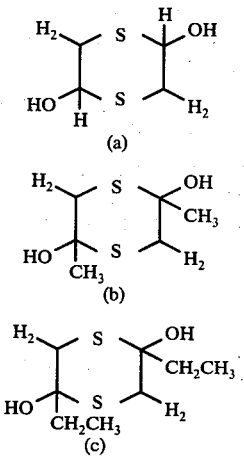

These compounds provide meat-like flavor for meatless edible compositions and also augment existing meat flavor in meat-containing foods. In this fashion, the dithianes of the type mentioned are especially suitable as flavorants. Foods containing no meat, but which are nutritionally equivalent to meat, can be made more acceptable by including such flavorants to provide the aroma and taste flavor of meat in addition to the appearance and nutrition desired. Where meats are used, the flavorant can maintain or augment the meat aroma and taste to thereby provide wider use of otherwise unusable meat portions. In this fashion, the flavorants can render more acceptable otherwise unacceptable, or acceptable - but not preferred, products.

A major problem with the use of the above dihydroxy-1,4 dithiane compounds is that they are not stable to the amount of heat used in food processing to a sufficient extent. These compounds break down to form the monomer under mild heat conditions as shown by the following reaction:

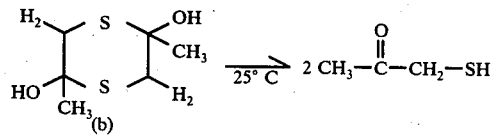

This is clearly shown by Katz and Wilson in *Flavor Ind.* Vol. 5, p 30, 1974 in which the dithiane at room temperature decomposes to its monomer.

The problems of the art are thus very clear.

SUMMARY OF THE INVENTION

Therefore, an object of this invention is to improve the flavor of food.

A further object of this invention is to provide a food having a stable flavor.

Yet another object of this invention is to provide a food having a flavorant with sufficient volatility.

Still another object of this invention is to provide a flavorant capable of surviving food processing conditions.

A further object of this invention is to provide a food having its flavor increased.

A still further object of this invention is to provide a food having a meaty aroma and taste.

These and other objects of this invention are achieved by adding to the food 1,8-dihydroxy-2,9-dithia-tricyclo[8.4.0.0$^{3,8}$]tetradecane or one of its derivatives which can vary, fortify, modify, enhance or improve the flavor and aroma of a foodstuff. Also, 1,7-dihydroxy-2,8-dithia-tricyclo[7.3.0.0$^{3,7}$]dodecane$^{(m)}$ and derivatives thereof may serve as a flavorant.

DESCRIPTION OF THE PREFERRED EMBODIMENTS

Meat flavor or aroma is imparted to foods by addition thereto of 1,8-dihydroxy-2,9-dithia-tricyclo[8.4.0.0$^{2,8}$]tetradecane$^{(e)}$ and derivatives thereof having the formula:

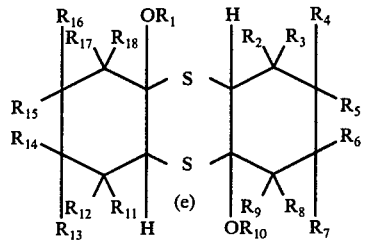

and 1,7-dihydroxy-2,8-dithia-tricyclo[7.3.0.0$^{3,7}$]dodecane$^{(m)}$ and derivatives thereof having the formula:

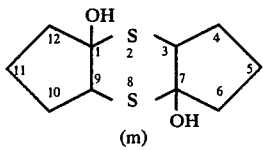

In the formulas as designated above, $R_2$ to $R_9$ and $R_{11}$ to $R_{18}$ are the same or different, and are an alkyl group containing 1 to 4 carbon atoms, hydrogen, or a hydroxyl group. $R_1$ and $R_{10}$ are the same or different, and are hydrogen, an alkyl group containing from 1 to 4 carbon atoms, an acetyl group, a phenacyl group, or a benzyl group.

As with any organic compound, there are a number of ways to name the compound. For example, the International Union of Pure and Applied Chemistry (IUPAC) names the compound of this type having R and R' equal to H in all cases 1,8-dihydroxy-2,9-dithia-tricyclo [8.4.0.0.$^{3,8}$] tetradecane. Another accepted name for the above compound, when R' and R are equivalent to H, is 2,3,5,6-Bis(tetramethylene)-2,5-dihydroxy-1,4-dithiane. Another acceptable name for the compound is octahydro-4a,9a(2 H,5aH)-thianthrenediol. The compound suitable for use as a flavorant for the purposes of this invention is named as the first given name — although all three names are equivalent and refer to the same compound. However, it is desired to use the first name of 1,8-dihydroxy-2,9-dithia-tricyclo [8.4.0.0.$^{3,8}$]tetradecane, because it is simpler to name the derivatives when R does not equal H and because this name is used by IUPAC.

The compounds above-referenced when added to a food provide a meat-like taste and aroma for the food when taken singly or in any combination. These compounds either provide meat flavor for food, augment meat flavor for food, or mask otherwise unacceptable flavoring for a food. These compounds, or mixtures thereof are customarily used in an amount effective to impart the desired flavor or aroma to the food. More specifically, up to about 2% by weight of the food comprises the compounds set forth. Even more specifically, about 0.0001% to 1% by weight of the food comprise these compounds. Most preferably, these compounds comprise 1 part per million to 100 parts per million by weight of the food. In this fashion, the most desirable flavor is imparted to the food.

An especially suitable compound of the type above-disclosed for use in this invention is the 1,8-dihydroxy-2,9-dithia-tricyclo[8.4.0.0$^{3,8}$]tetradecane$^{(f)}$. This compound provides a beefy, meaty, and spicy type of aroma which is extremely suitable for the purposes of this invention.

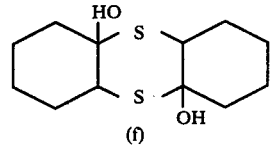

The above compound may be modified by making the acetate ester, the benzoate ester, or the benzylether as depicted in (g), (h), and (i) respectively by substituting the appropriate group for R' on the oxygen atom which is bonded to carbon atoms 1 and 8.

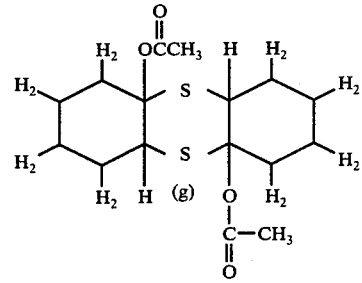

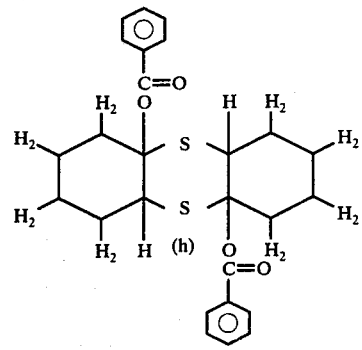

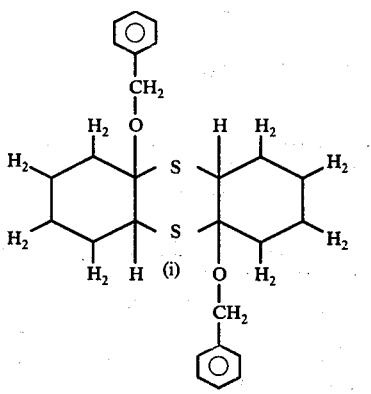

Another suitable compound depicted in (j)

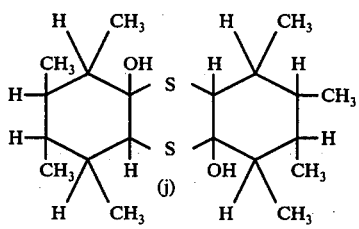

called 4,5,6,7,11,12,13,14-octamethyl-1,8-dihydroxy-2,9-dithia-tricyclo[8.4.0.0.$^{3,8}$]tetradecane is also a meat or beef flavorant.

Other suitable compounds are depicted in (k), (l), and (m).

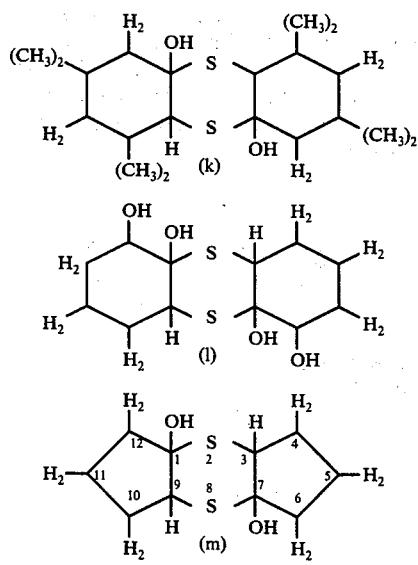

These compounds are called 4,4,6,6,11,11,13,13-octamethyl-1,8-dihydroxy-2,9-dithia-tricyclo[8.4.0.0$^{3,8}$]tetradecane$^{(k)}$, 1,7,8,14-tetrahydroxy-2,9-dithia-tricyclo[8.4.0.0$^{3,8}$]tetradecane$^{(l)}$ and 1,7-dihydroxy-2,8-dithia-tricyclo[7.3.0.0$^{3,7}$]dodecane$^{(m)}$ respectively, and are beef flavors.

It is especially preferred, that groups on $C_1$ be the same as $C_8$; $C_4$ be the same as $C_{11}$; $C_5$ be the same as $C_{12}$; $C_6$ be the same as $C_{13}$; and $C_7$ be the same as $C_{14}$. This requirement simplifies the isolation of a pure compound of a particular type. Otherwise, mixed concoctions of different compounds are achieved and the desired results of this invention and the flavorants are not as easily predictable. Especially suitable compounds for the purpose formed herein of this invention are 2,5-dihydroxy-1,4-dithianes.

The compounds described in this application may be used singly or in admixtures comprising two or more thereof. The formulation may combine additional flavoring materials such as furfural, benzaldehyde, and hexanal to simulate a wide variety or organoleptic characteristics. In addition, its derivatives may be admixed with one or more flavorant adjuvants such as stabilizers, thickeners, surface active agents, conditioners, flavorants and flavor intensifiers to provide suitable flavor imitative of roasted meats of various types.

The compounds described in this application can be added to the foods to be flavored by any conventional techniques. Typical conventional techniques include spray drying, blending, stirring, dissolving and the like. The addition of these compounds is carried out in any stage of the preparation of the foodstuff to which the compounds are to be applied.

These flavorants can be added to almost any type of food, but are particularly applicable to pet foods of the moist, semi-moist or dry type. Typical pet foods which may use the particular flavorants are disclosed in U.S. Pat. No. 3,922,353 to Bernotavicz, U.S. Pat. No. 3,380,832 to Bone, U.S. Pat. No. 3,738,847 to Bechtel, U.S. Pat. No. 3,883,672 to Bone and Shannon, U.S. Pat. No. 3,974,296 to Burkwall, and U.S. Pat. No. 3,984,576 to Burkwall, Leyh, and Reagan. The referenced patents are incorporated herein by reference.

The following examples are presented for the purposes of illustrating the invention without unduly limiting the invention. All parts and percentages in the examples and throughout the specification are by weight unless otherwise specified. The preparation of the compounds suitable for use as flavorants in this invention is described in Volume 52, (1957) of the *Chemical Abstracts* at Columns 1174, and 1175, at which point is abstracted an article by Asinger, et al. Similarly, other derivatives suitable for use as flavorants in this invention and their methods of preparation are described in Volume 61, (1966) of *Chemical Abstracts* at Columns 1854 and 1855 wherein another article by Asinger et al. is abstracted. Both of these abstracts and the corresponding articles are incorporated herein by reference.

EXAMPLE 1

The compound 1,8-dihydroxy-2,9-dithia-tricyclo[8.4.0.0$^{3,8}$]tetradecane$^{(f)}$ is prepared as follows: To a 250 milliliter 3-necked round bottom flask equipped with a mechanical stirrer, an addition funnel, and a gas inlet tube are added sodium (4.6 grams) and ethanol (100 milliliters). The solution is saturated with hydrogen sulfide at −15° C. and with vigorous stirring. To this solution is added 2-chlorocyclohexanone (6.7 grams) in a 1:1 ethanol-ether solvent. The addition is carried out slowly with vigorous stirring and continuing addition of hydrogen sulfide at a temperature of −10° C. over a 24 minute period. The mixture is stirred for an additional 10 minutes while maintaining the mixture at 0° C. The resulting precipitate is filtered and washed with warm water. The crude precipitate is then recrystallized from chloroform yielding 5.3 grams of product which is a 41% yield. Under a standard, infrared spectroscopy testing process, the pure product in a potassium bromide pellet has infrared spectrum peaks at 3325 cm$^{-1}$ indicating an O-H stretch, 2920 and 2850 cm$^{-1}$ indicating a C-H stretch, 1360 cm$^{-1}$ indicating an O-H bend and 1183 cm$^{-1}$ indicating a C—O stretch. A melting point of 145° C. combines with infrared spectroscopy data to confirm the structure. This high melting point also shows that the compound would be thermally stable under the process conditions and to produce either dry pet foods usually processed at 95°–140° C, semi-moist pet foods, usually processed at 75°–110° and canned pet foods usually processed at 95°–120° C.

EXAMPLE 2

The flavoring of Example 1 is topically applied to a commercial semi-moist pet food. Then two days of tests are conducted using dogs as the test animals to compare preference of the control product containing no flavorant and the same product containing the product of Example I invention in the amount of 15 ppm. The dogs used are of varying size and breed. The results of these tests shown below indicate excellent palatability of the product containing 1,8-dihydroxy-2,9-dithia-tricyclo[8.4.0.0$^{3,8}$]tetradecane at 15 ppm level. Using standard methods of statistical analysis, the experimental product containing the 15 ppm flavorant was judged to be highly significantly preferred over control product containing no flavorant.

|       | % Consumed |                          |
|-------|------------|--------------------------|
|       | Control    | Test with 15 ppm flavorant |
| Day 1 | 25         | 75                       |
| Day 2 | 24         | 76                       |

EXAMPLE III

When the product of Example I, 1,8-dihydroxy-2,9-dithia-tricyclo[8.4.0.0$^{3,8}$]tetradecane, was topically applied on a commercial dry dog food rehydrated with 65% water, significant palatability was achieved at the following levels:

|        | Average % Consumed Test Material | Average % Consumed Control |
|--------|----------------------------------|----------------------------|
| 6 ppm  | 57%                              | 43%                        |
| 15 ppm | 66%                              | 34%                        |

-continued

|        | Average % Consumed Test Material | Average % Consumed Control |
|--------|----------------------------------|----------------------------|
| 30 ppm | 71%                              | 29%                        |

Again this shows that the flavorant has excellent palatability and that the palatability in this case is approximate linear with concentration.

Having now fully described and disclosed this new invention, what is claimed and sought to be secured by Letters Patent of the United States is:

1. A process for altering the flavor of a foodstuff comprising adding to the foodstuff an amount of a flavorant 1,7-dihydroxy-2,8-dithia-tricyclo[7.3.0.0$^{3,7}$]dodecane effective to impart a meat flavor and represented by the formula:

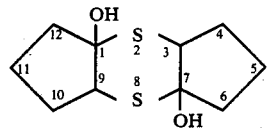

2. The process of claim 1 wherein the flavorant is added in an amount sufficient to impart a meat-like flavor and comprises up to 2 percent by weight of the pet food.

3. The process of claim 2 wherein the amount of flavorant is 0.0001 to 1 percent by weight of the pet food.

4. The process of claim 3 wherein the amount of flavorant is 1 to 100 parts per million by weight of the pet food.

5. A pet food comprising an edible foodstuff and a flavorant, wherein the flavorant comprises an amount of 1,7-dihydroxy-2,8-dithia-tricyclo [7.3.0.0$^{3,7}$] dodecane effective to impart a meat flavor, the flavorant being up to 2 percent by weight of the food, and represented by the formula:

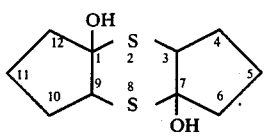

6. The pet food of claim 5 wherein the amount of flavorant is 0.0001 to 1 percent by weight of the food.

7. The pet food of claim 6 wherein the amount of flavorant is 1 to 100 parts per million by weight of the food.

* * * * *

UNITED STATES PATENT OFFICE
CERTIFICATE OF CORRECTION

PATENT NO. : 4,107,342
DATED : August 15, 1978
INVENTOR(S) : Michael J. Greenberg It is certified that error appears in the above-identified patent and that said Letters Patent are hereby corrected as shown below:

In the title "FLAVORING WITH 1,7-DIHYDROXY-2,5-DITHIA-TRICYCLO[7.3.0.0$^{3,7}$]DODECANE" should read

--FLAVORING WITH 1,7-DIHYDROXY-2,8-DITHIA-TRICYCLO[7.3.0.0$^{3,7}$]DODECANE--

Signed and Sealed this

Fifth Day of June 1979

[SEAL]

Attest:

RUTH C. MASON
Attesting Officer

DONALD W. BANNER
Commissioner of Patents and Trademarks